US006784302B2

(12) United States Patent
Katsuki et al.

(10) Patent No.: US 6,784,302 B2
(45) Date of Patent: Aug. 31, 2004

(54) METHOD OF PRODUCING OPTICALLY ACTIVE LACTONE COMPOUND AND COMPLEX USED IN THE METHOD

(75) Inventors: Tsutomu Katsuki, Fukuoka (JP); Akira Watanabe, Kurme (JP); Tatsuya Uchida, Fukuoka (JP)

(73) Assignee: Kyushu University, Fukuoka (JP)

( * ) Notice: Subject to any disclaimer, the term of this patent is extended or adjusted under 35 U.S.C. 154(b) by 0 days.

(21) Appl. No.: 10/405,603

(22) Filed: Apr. 3, 2003

(65) Prior Publication Data

US 2004/0010152 A1 Jan. 15, 2004

(30) Foreign Application Priority Data

Apr. 11, 2002 (JP) ....................... 2002-109617
Mar. 27, 2003 (JP) ....................... 2003-087186

(51) Int. Cl.[7] ........................... C07D 307/93; C07F 7/00
(52) U.S. Cl. ....................... 549/302; 502/171; 502/150; 502/160; 502/200; 502/349; 549/295; 549/300; 549/311; 544/64; 544/89
(58) Field of Search .................. 549/302, 300, 549/311, 295; 502/171, 150, 160, 200, 349; 544/64, 89

(56) References Cited

PUBLICATIONS

Bolm et al., "Optically Active Lactones from a Bacyer–Villiger–Type Metal–Catalyzed Oxidation with Molecular Oxygen," Angew. Chem. Int. Ed. Engl., 33, No. 18, pp. 1848–1849, 1994.
Gusso et al., "Platinum–Catalyzed Oxidations with Hydrogen Peroxide: Enantiospecific Baeyer–Villiger Oxidation of Cyclic Ketones," Organometallics 13, pp. 3442–3451, 1994.
Bolm et al., "Enantioselective Metal–catalyzed Baeyer–Villiger Oxidation of Cyclobutanones," Synlett,, pp. 1151–1152, Oct. 1997.
Bolm et al., "Enantioselective Baeyer–Villiger Oxidations Catalyzed by Chiral Magnesium Complexes," Synlett, No. 9, pp. 1461–1463, 2001.
Bolm et al., "Chiral aluminum complexes as catalysts in asymmetric Baeyer–Villiger reactions of cyclobutanones," Can J. Chem. 79, pp. 1593–1597, 2001.

Uchida et al. "Cationic Co (III)(salen)–catalyzed enantioselective Baeyer–Villiger oxidation of 3–arylcyclobutanones using hydrogen peroxide as a terminal oxidant," Tetrahedron Letters 42, pp. 6911–6914, 2001.

A. Phillips et al., "Synthesis of γ–Butyrolactones by a Baeyer–Villiger Oxidation with Hydrogen Peroxide, Catalysed By Methyltrioxorhenium," *European of Journal of Organic Chemistry*, vol. 8, pp. 1767–1770, 1999.

T. Uchida et al., "Cationic Co(III)(salen)–Catalyzed Enantioselective Baeyer–Villiger Oxidation of 3–Arylcyclobutanones Using Hydrogen Peroxide as a Terminal Oxidant," *Tetrahedron Letters, Elsevier Science Publishers*, Amsterdam, vol. 42, No. 30, pp. 6911–6914, 2001.

A. Watanabe et al., "Highly Enantioselective Baeyer–Villiger Oxidation using Zr(salen) Complex as Catalyst," *Tetrahedron Letters, Elsevier Science Publishers*, Amsterdam vol. 43, No. 25, pp. 4481–4485, 2002.

*Primary Examiner*—Charanjit S. Aulakh
(74) *Attorney, Agent, or Firm*—Oliff & Berridge, PLC

(57) ABSTRACT

An optically active lactone compound is produced by using a Zr(salen) complex of the following formula (I) or its enantiomer as a catalyst and subjecting a cyclic ketone compound to a Baeyer-Villiger reaction with at least one oxidizer selected from hydrogen peroxide, aqueous hydrogen peroxide and urea-hydrogen peroxide adduct in a solvent:

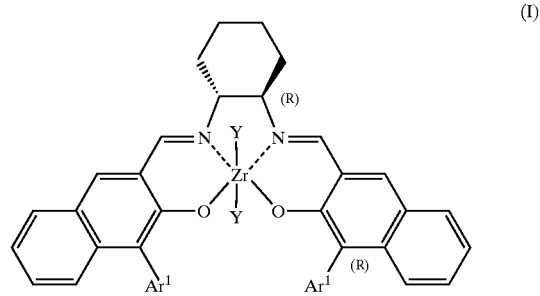

wherein $Ar^1$ is an aryl group having a carbon number of 10 to 16 and Y is a phenoxy group or an alkoxy group having a carbon number of 1 to 10.

16 Claims, No Drawings

METHOD OF PRODUCING OPTICALLY ACTIVE LACTONE COMPOUND AND COMPLEX USED IN THE METHOD

BACKGROUND OF THE INVENTION

1. Field of the Invention

This invention relates to a method of producing an optically active lactone compound and a Zr(salen) complex suitable for this method.

2. Description of Related Art

The Baeyer-Villiger reaction, i.e. oxidative conversion of carbonyl to ester (or lactone) is of high synthetic value and is widely used in various syntheses. Although many biocatalyzed asymmetric Baeyer-Villiger reactions are known, their chemical versions are still limited in number.

In 1994 is reported copper-catalyzed asymmetric Baeyer-Villiger reaction by Bolm et al (Bolm C., Schlingloff G. and Weickhardt K., Angew. Chem. Int. Ed. Engl. 1994, 33, 1848–1849). In the same year is reported platinum-catalyzed asymmetric Baeyer-Villiger reaction by Strukul et al (Gusso A., Baccin C., Pinna F. and Strukul G., Organometallics, 1994, 13, 3442–3451).

Since then, several catalysts are used in the asymmetric Baeyer-Villiger reaction, and high enantioselectivity is realized in the Baeyer-Villiger reactions of some limited substrates (Bolm C., Luong K. K. and Schlingloff G., Synlett., 1997, 1151–1152; Bolm C., Beckmann O., Cosp A. and Palazzi C., Synlett., 2001, 1461–1463; and Bolm C., Beckmann O. and Palazzi C., Can. J. Chem., 2001, 79, 1593–1597). However, it is strongly demanded to introduce new methodology into the asymmetric Baeyer-Villiger reaction.

The Baeyer-Villiger reaction is a two-step reaction: (i) nucleophilic addition of an oxidizer producing Criegee adduct and (ii) rearrangement of the adduct to ester (or lactone). If a carbonyl compound is a pro-chiral cyclic compound as a starting substance, a product through the Baeyer-Villiger reaction is a pair of enantiomeric lactones.

The stereochemistry of the Baeyer-Villiger reaction is depended by two factors: (i) face selectivity in oxidizer addition and (ii) enantiotopos selectivity in migration. However, as the formation of Criegee adduct is a reversible reaction and the migration of the adduct to lactone is an irreversible reaction and a rate-determining step, topos-selection in the migration step is considered to strongly influence the stereochemistry of the Baeyer-Villiger reaction.

The migration is largely influenced by interaction between σ-orbital of migrating C—C bond and σ*-orbital of O—O bond as mentioned below. For this end, it is considered to achieve a high enantioselectivity if σ-bond and σ*-bond are topos-selectively interacted with each other. Also, it is considered to realize the topos-selective interaction if the Criegee adduct makes a chelate and the chelate conformation is regulated appropriately. Therefore, a metallosalen complex of cis-β structure is considered to be a catalyst suitable for realizing the topos-selective interaction because it provides two neighboring coordinating sites for the chelate formation and its metal center is chiral.

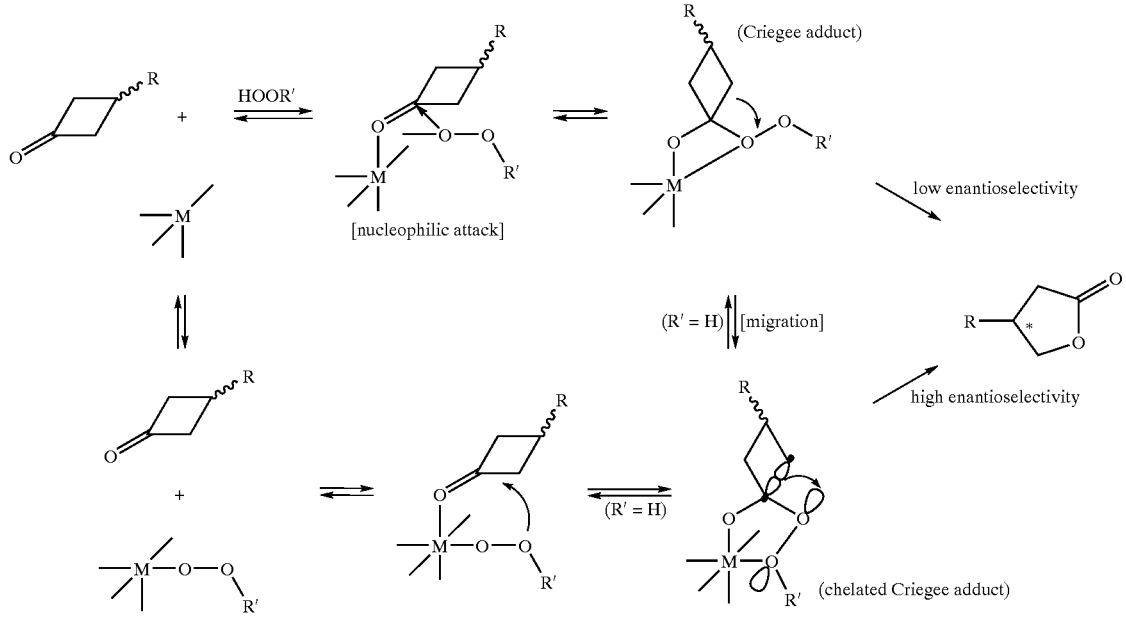

Based on the above theory, the inventors have reported that Co(salen) complex of square planar geometry does not show any enantioselectivity in the Baeyer-Villiger reaction of 3-substituted cyclobutanone, while Co(salen) complex having a cis-β structure shows a good enantioselectivity up to an enantiomeric excess of 78%ee (Uchida T. and Katsuki T., Tetrahedron Lett., 2001, 42, 6911–6914).

However, the above result that the enantiomeric excess of the product is not more than 78% ee means that the control of chelate conformation by the Co(salen) complex of cis-β structure is not sufficient.

SUMMARY OF THE INVENTION

It is, therefore, an object of the invention to provide a method of producing an optically active lactone compound capable of further enhancing the enantiomeric excess. Also, it is another object of the invention to provide a catalyst suitable for the method of producing such a lactone compound.

The inventors have made various studies in order to achieve the above objects and found that a lactone compound can be produced in a higher enantiomeric excess by synthesizing a specified Zr(salen) complex and using such a complex as a catalyst to conduct a Baeyer-Villiger reaction of a cyclic ketone compound.

According to a first aspect of the invention, there is the provision of a method of producing an optically active lactone compound, which comprises using a Zr(salen) complex represented by the following formula (I) or (II):

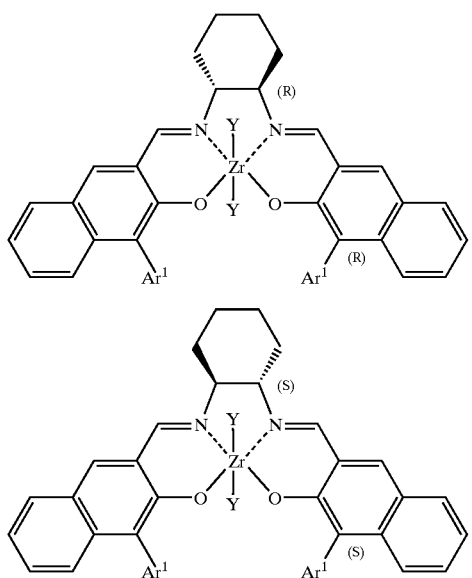

wherein $Ar^1$ is an aryl group having a carbon number of 10 to 16 and Y is a phenoxy group or an alkoxy group having a carbon number of 1 to 10 as a catalyst in a solvent, and conducting a Baeyer-Villiger reaction of a cyclic ketone compound with at least one oxidizer selected from the group consisting of hydrogen peroxide, aqueous hydrogen peroxide and urea-hydrogen peroxide adduct (UHP).

The preferable embodiments of the production method according to the invention are as follows.

The Zr(salen) complex is represented by the following formula (III) or (IV):

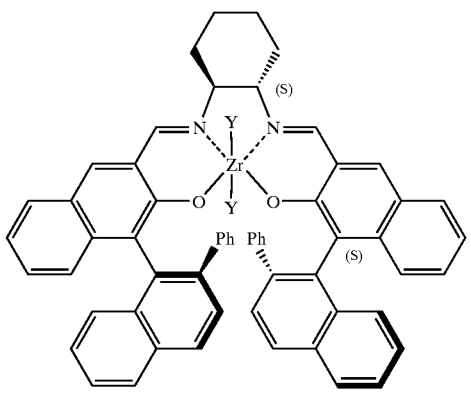

wherein Ph is a phenyl group and Y is the same meaning as mentioned above.

The symbol Y is a phenoxy group.

The cyclic ketone compound is represented by the following formula (V), (VI), (VII), (VIII) or (IX):

wherein $R^1$ is a substituted or non-substituted alkyl group having a carbon number of 1 to 20 or a substituted or non-substituted aryl group having a carbon number of 6 to 15,

wherein $R^2$ is a substituted or non-substituted alkyl group having a carbon number of 1 to 20 or a substituted or non-substituted aryl group having a carbon number of 6 to 15,

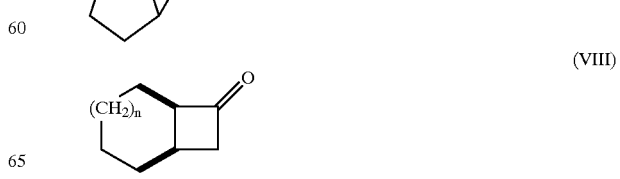

wherein n is 0, 1 or 2,

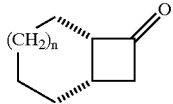
(IX)

wherein n is 0, 1 or 2.

The cyclic ketone compound is 3-phenyl cyclobutanone, 3-(p-chlorophenyl) cyclobutanone, 3-(p-methoxyphenyl) cyclobutanone or 3-octyl cyclobutanone.

The lactone compound is represented by the following formula (X), (XI), (XII), (XIII), (XIV), (XV) or (XVI):

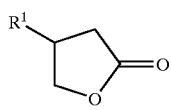
(X)

wherein $R^1$ is the same meaning as mentioned above,

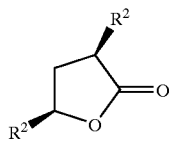
(XI)

wherein $R^2$ is the same meaning as mentioned above,

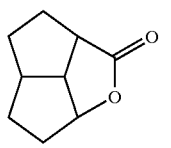
(XII)

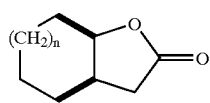
(XIII)

wherein n is 0, 1 or 2,

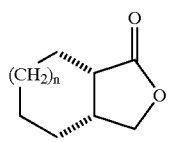
(XIV)

wherein n is 0, 1 or 2,

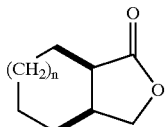
(XV)

wherein n is 0, 1 or 2,

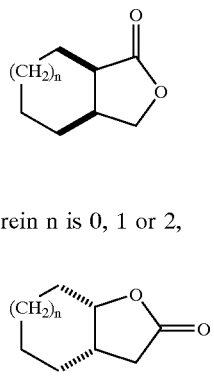
(XVI)

wherein n is 0, 1 or 2.

The lactone compound is β-phenyl-γ-butyrolactone, β-(p-chlorophenyl)-γ-butyrolactone, β-(p-methoxyphenyl)-γ-butyrolactone or β-octyl-γ-butyrolactone.

The solvent is a halogenated hydrocarbon. This halogenated hydrocarbon is dichloromethane or chlorobenzene.

The oxidizer is a urea-hydrogen peroxide adduct (UHP).

The lactone compound has an enantiomeric excess of not less than 80%ee.

According to a second aspect of the invention, there is the provision of a Zr(salen) complex represented by the following formula (I) or (II):

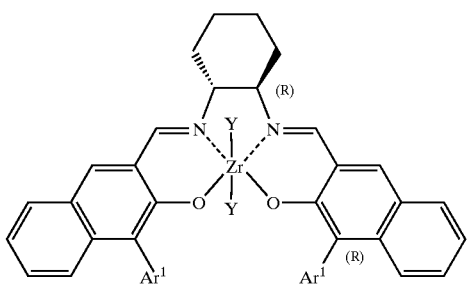
(I)

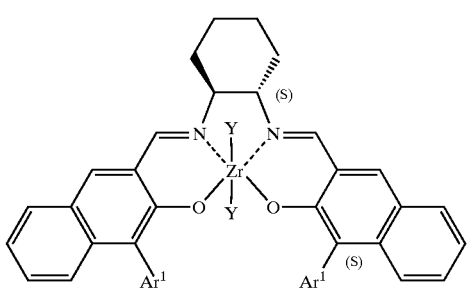
(II)

wherein $Ar^1$ and Y are the same meanings as mentioned above.

The preferable embodiments of the second aspect of the invention are as follows.

The Zr(salen) complex is represented by the following formula (III) or (IV):

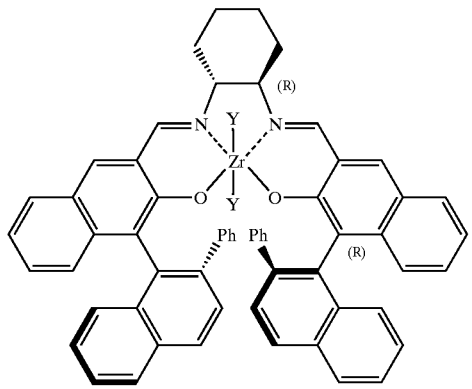

(III)

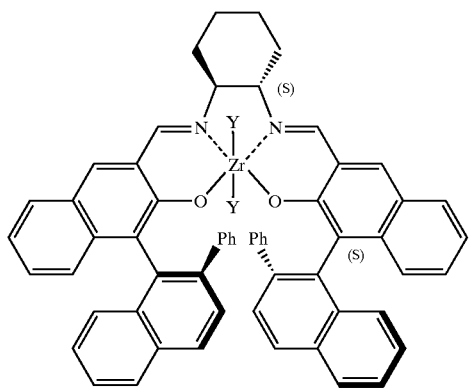

(IV)

wherein Ph and Y are the same meanings as mentioned above.

The symbol Y is a phenoxy group.

DETAILED DESCRIPTION OF THE INVENTION

The invention will be described in detail below. The Zr(salen) complex according to the invention is represented by the formula (I) or (II):

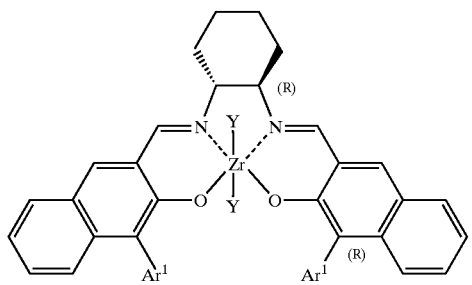

(I)

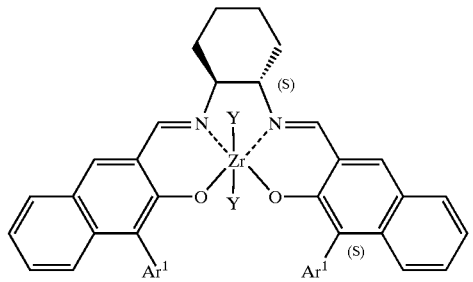

(II)

wherein $Ar^1$ is an aryl group having a carbon number of 10 to 16 and Y is phenoxy group or an alkoxy group having a carbon number of 1 to 10.

The complex used in the production method of the invention is important that a metal center is Zr. Although the inventors have examined a Ti(salen) complex having Ti as a metal center among the same Group 4A of the Periodic Table, it has been confirmed that this complex hardly shows a catalytic activity. Because Ti is strong in the oxophilicity as compared with Zr, and when the Ti(salen) complex is treated with hydrogen peroxide or UHP, it produces a peroxy titanium(salen) complex as shown below. Also, the ring-opening of the peroxy Ti(salen) complex is slow.

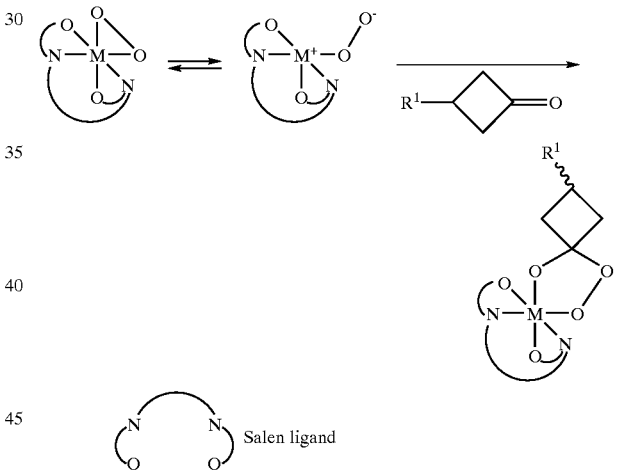

On the other hand, Zr is weak in the oxophilicity as compared with Ti and Zr—O bond is longer than Ti—O bond, so that it is considered that the ring-opening of peroxy Zr(salen) complex is much easier, or the hydroperoxo group coordinated to the zirconium ion is reluctant to generate a peroxy Zr(salen) complex. Thus, Zr(salen) complexes are expected to promote the Baeyer-Villiger reaction.

As the aryl group having a carbon number of 10 to 16 in $Ar^1$ of the formula (I) or (II), mention may be made of 1-naphthyl group, 2-biphenyl group, 2-phenyl-1-naphthyl group, 2-methyl-1-naphthyl group, 2-[3,5-dimethylphenyl]-1-naphthyl group, 2-[4-methylphenyl]-1-naphthyl group, 2-{4-[t-butyldiphenyl-silyl]phenyl}-1-naphthyl group, 2-methoxy-1-naphthyl group and so on. Among them, 2-phenyl-1-naphthyl group is preferable in view of the catalytic activity and enantioselectivity in the asymmetric Baeyer-Villiger reaction. In this case, the Zr(salen) complex is represented by the following formula (III) or (IV):

(III)

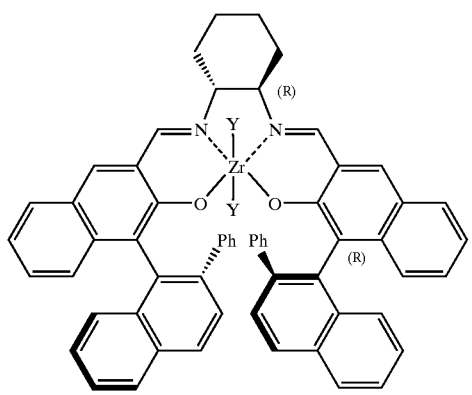

(IV)

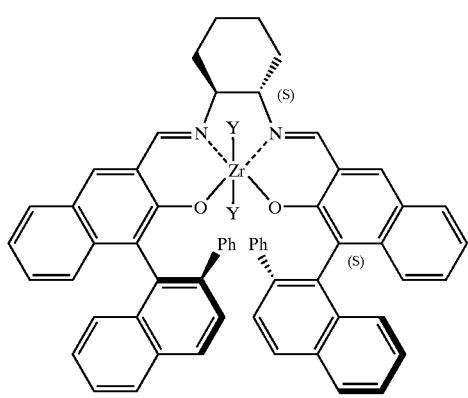

The Zr(salen) complex has two Ys in its apical position, in which Y is a phenoxy group or an alkoxy group having a carbon number of 1 to 10. As the alkoxy group having a carbon number of 1 to 10, mention may be made of methoxy group ($CH_3O$), ethoxy group ($C_2H_5O$), n-propoxy group (n-$C_3H_7O$), isopropoxy group (($CH_3$)$_2$CHO), cyclohexyloxy group (c-$C_6H_{11}O$), n-octyloxy group (n-$C_8H_{17}O$) and so on. Among them, the phenoxy group is preferable as Y in view of the catalytic activity and enantioselectivity in the asymmetric Baeyer-Villiger reaction.

When the Zr(salen) complex is used as a catalyst in the asymmetric Baeyer-Villiger reaction, an amount to be used is a range of 1 to 10 mol %, preferably 4 to 6 mol % per 1 mol of a cyclic ketone as a substrate.

The phenoxy group of the Zr(salen) complex is readily replaced by other alkoxy, carbonyl or their equivalent group. In the Baeyer-Villiger reaction, oxygen atom in carbonyl group of a substrate and oxygen atom in an oxidizer are simultaneously coordinated to these coordinating sites. The apical ligands (Y) of the Zr(salen) complex can be easily replaced with the carbonyl group of the substrate or the oxygen atom in the oxidizer. Such coordinated state is kept up to the completion of the reaction. Therefore, there are improved the face selectivity in the nucleophilic attack of the oxygen atom in the oxidizer to carbon in the carbonyl group to give a Criegee adduct and the enatiotopos selectivity in the migration from the Criegee adduct produced by the nucleophilic attack. Since the migration is an irreversible reaction and the rate-determining step as previously mentioned, the height of enantiotopos selectivity in the migration step is largely reflected in the enantiomeric excess of the product.

The cyclic ketone compound used in the invention is a pro-chiral cyclic ketone compound producing an asymmetric carbon through the Baeyer-Villiger reaction, which includes, for example, compounds represented by the following formulae (V), (VI), (VII), (VIII), (IX) and so on.

(V)

wherein $R^1$ is a substituted or non-substituted alkyl group having a carbon number of 1 to 20 or a substituted or non-substituted aryl group having a carbon number of 6 to 15, (VI)

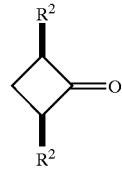

wherein $R^2$ is a substituted or non-substituted alkyl group having a carbon number of 1 to 20 or a substituted or non-substituted aryl group having a carbon number of 6 to 15, (VII)

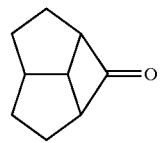

(VIII)

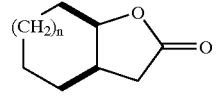

wherein n is 0, 1 or 2, (IX)

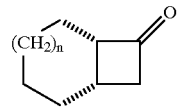

wherein n is 0, 1 or 2.

As the alkyl group in $R^1$ of the formula (V), mention may be made of methyl, ethyl, propyl, isopropyl, butyl, isobutyl, t-butyl, pentyl, isopentyl, neopentyl, hexyl, heptyl, octyl, 2-ethylhexyl, nonyl, decyl, undecyl, dodecyl, tridecyl, isotridecyl, myristyl, palmityl, stearyl, icosyl, docosyl and so on.

As the aryl group in $R^1$ of the formula (V), mention may be made of phenyl, tolyl, xylyl, cumenyl, mesityl, ethylphenyl, propylphenyl, butylphenyl, pentylphenyl, hexylphenyl, heptylphenyl, octylphenyl, nonylphenyl, α-naphthyl, β-naphthyl and so on.

Each of the above alkyl group and aryl group may be substituted with a halogen, an alkoxy group having a carbon number of 1 to 4 or the like.

The alkyl group and aryl group in $R^2$ of the formula (VI) are the same as mentioned in $R^1$ of the formula (V). Also, each of the alkyl group and aryl group may be substituted with a halogen, an alkoxy group having a carbon number of 1 to 4 or the like.

The oxidizer used in the invention is hydrogen peroxide or urea-hydrogen peroxide adduct (UHP). In this case, hydrogen peroxide may be used as an aqueous solution. The oxygen atom in such an oxidizer coordinates in the metal center of the Zr(salen) complex and nucleophilic-attacks to carbon in carbonyl group of a substrate to form a chelated Criegee adduct. Alternatively, the Criegee adduct is formed by nucleophilic-attacking to carbonyl group coordinated to the metal center and then chelated. On the contrary, when t-butyl hydrogen peroxide (TBHP) or bis(trimethylsilyl) peroxide is used as an oxidizer, the presence of bulky t-butyl group or silyl group retards the chelate formation of the Criegee adduct and hence the enantioselectivity in the reaction remarkably lowers. Among the above oxidizers, the urea-hydrogen peroxide adduct (UHP) is preferable in view of the improvement of the enantiomeric excess in the product. The amount of the oxidizer used is within a range of 1-2 equivalent, preferably 1.2-1.3 equivalent per the cyclic ketone as the substrate.

The product of the invention, optically active lactone compound is produced by the asymmetric Baeyer-Villiger reaction of the pro-chiral cyclic ketone compound. In the production method of the invention is obtained the optically active lactone compound because the enantiotopos selectivity in the migration are high as previously mentioned. The optically active lactone compound obtained by the production method of the invention corresponds to the aforementioned cyclic ketone and includes, for example, compounds represented by the following formulae (X), (XI), (XII), (XIII), (XIV), (XV), (XVI) and so on. Moreover, optically active lactone enantiomers are obtained by properly using the Zr(salen) complex of the formula (I) and the Zr(salen) complex of the formula (II).

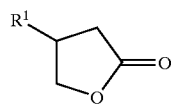
(X)

wherein R¹ is the same meaning as mentioned above,

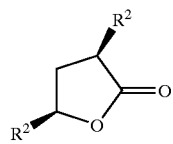
(XI)

wherein R² is the same meaning as mentioned above,

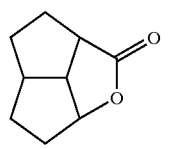
(XII)

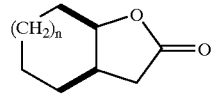
(XIII)

wherein n is 0,1 or 2,

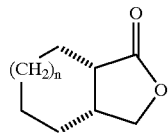
(XIV)

wherein n is 0, 1 or 2,

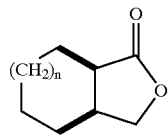
(XV)

wherein n is 0, 1 or 2,

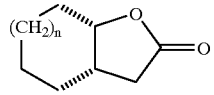
(XVI)

wherein n is 0, 1 or 2.

As the lactone corresponding to the cyclic ketone of the formula (VIII), the lactone of the formula (XV) is considered in addition to the lactone of the formula (XI), but when the Zr(salen) complex of the formula (I) is used as a catalyst, the lactone of the formula (XV) hardly produces. Also, as the lactone corresponding to the cyclic ketone of the formula (IX), the lactone of the formula (XVI) is considered in addition to the lactone of the formula (XIV), but when the Zr(salen) complex of the formula (I) is used as a catalyst, the amount of the lactone of the formula (XVI) produced is smaller than that of the lactone of the formula (XIV). For example, when n in the formula (IX) is 1, the amount of the lactone of the formula (XVI) produced is about ⅙ of that of the lactone of the formula (XIV), while when n is 0, the lactone of the formula (XVI) hardly produces.

On the other hand, when the enantiomer of the Zr(salen) complex of the formula (I), i.e. the Zr(salen) complex of the formula (II) is used as a catalyst, the lactone of the formula (XVI) is selectively obtained from the cyclic ketone of the formula (IX) and the lactone of the formula (XIV) hardly produces. Also, the lactone of the formula (XV) is mainly obtained from the cyclic ketone of the formula (VIII). For example, when n in the formula (VIII) is 1, the amount of the lactone of the formula (XIII) is about ⅙ of that of the lactone of the formula (XV), while when n is 0, the lactone of the formula (XIII) hardly produces.

Further, when a relative reaction ratio of the cyclic ketone of the formula (VIII) to the cyclic ketone of the formula (IX) is calculated according to the following Kagan's equation, it is about 4 in case that n in the formulae (VIII) and (IX) is 1, and about 2 in case that n is 0.

$$k_R/k_S = \ln(1-\text{conversion})(1-ee_S)/\ln(1-\text{conversion})(1+ee_S) \qquad \text{Kagan's equation}$$

wherein $k_R$ is a reaction rate constant when R-isomer ($S_R$) of the substrate is converted into a reaction product ($P_R$), $k_S$ is a reaction rate constant when S-isomer of the substrate ($S_S$) is converted into a reaction product ($P_S$), and $ee_S$ is an enantiomeric excess of the substrate. Also, a reaction rate of the cyclic ketone of the formula (VIII) is faster than that of the cyclic ketone of the formula (IX). Therefore, a kinetically division is possible when using a racemic mixture of the cyclic ketone of the formula (VIII) and the cyclic ketone of the formula (IX) as a substrate.

The production method according to the invention is carried out in a solvent. As the solvent, mention may be made of a halogenated hydrocarbon such as dichloromethane, chlorobenzene or the like; an ether compound such as diethyl ether or the like; an alcohol compound such as ethanol or the like; and an ester compound such as ethyl acetate or the like. Among them, the halogenated hydrocarbon such as dichloromethane, chlorobenzene or the like is preferable in view of the improvement of the reaction rate in the asymmetric Baeyer-Villiger reaction and the enantioselectivity. The amount of the solvent used is within a range of 1 to 20 ml, preferably 8 to 10 ml per 1 mmol of the cyclic ketone as the substrate.

The enantiomeric excess used as a measure for the purity of the optically active isomer in the invention is represented by the following equation:

$$\text{Enantiomeric excess } (\%ee) = [\alpha]_D \times 100/[\alpha]_{Dmax} = (R-S) \times 100/(R+S)$$

or $$(S-R) \times 100/(R+S)$$

wherein $[\alpha]_D$ is a specific angle of rotation of a sample, $[\alpha]_{Dmax}$ is a specific angle of rotation of an optically pure substance, R is a ratio of R-isomer occupied in the sample, and S is a ratio of S-isomer occupied in the sample. When the ratios of R-isomer and S-isomer are the same or a racemate, the enantiomeric excess is 0%ee. The enantiomeric excess of the reaction product can be measured by means of a high-speed liquid chromatography (HPLC) or a gas-liquid chromatography (GLC) using an optically active column.

The production method according to the invention is preferable to be carried out at 0 to 60° C. The reaction temperature is more preferable to be 0 to 40° C. from a viewpoint of the enantiomeric excess. When the reaction temperature is lower than 0° C., the reaction rate is slow, while when it exceeds 60° C., the enantiomeric excess lowers.

In the invention, the optically active lactone compound can be produced by stirring a mixed solution of the cyclic ketone compound, the oxidizer, the solvent and the catalyst. The stirring method is not particularly limited so long as the uniformity of the mixed solution is ensured, so that any well-known methods can be applied. Also, the reaction time is not particularly limited and is properly selected in accordance with the reaction temperature. It is preferable that when the reaction temperature is high, the reaction time is short, while when the reaction temperature is low, the reaction time is long.

The following examples are given in illustration of the invention and are not intended as limitations thereof.

Complex Synthesis Example 1

(1R, 2R)-1,2-cyclohexanediamine (made by Kankyo Kagaku Center Co., Ltd., 57 mg, 0.5 mmol) is dissolved into ethanol (10 ml). To the resulting solution is added (R)-3-formyl-2-hydroxy-2'-phenyl-1,1'-binaphthyl (374 mg, 1.0 mmol). Moreover, (R)-3-formyl-2-hydroxy-2'-phenyl-1,1'-binaphthyl is obtained by a well-known method described in H. Sakaki, R. Irie, T. Hamada, K Suzuki and T. Katsuki, Tetrahedron, 50(41), 11827–11838 (1994) or the like. This solution is refluxed under heating for 6 hours with stirring. After the completion of the reaction, the temperature is turned to room temperature, and the resulting precipitates are filtered and dried by heating under a reduced pressure for 1 hour. Then, the dried precipitates are dissolved into anhydrous tetrahydrofuran (15 ml) under a nitrogen atmosphere and added with sodium hydride (oily, about 60%) (made by Kishida Kagaku Co., Ltd., 44.0 mg, 1.1 mmol) and stirred for 1 hour. The reaction solution is added with a 1:2 complex of zirconium chloride-tetrahydrofuran (made by Aldrich Chem. Co., 311 mg, 0.8 mmol) and further stirred for 12 hours and concentrated in a rotary evaporator to remove tetrahydrofuran. After precipitates produced by adding toluene to the resulting residue is filtered off on Celite (trade mark, made by Jhons-Manville Corp.), the filtrate is concentrated and subsequently dried by heating under a reduced pressure for 1 hour. The dried concentrate is dissolved into tetrahydrofuran (10 ml) under a nitrogen atmosphere. The resulting solution is added with lithium phenoxide (in 1.0M tetrahydrofuran)(made by Aldrich Chem. Co., 1.0 ml, 1.0 mmol) and stirred for 16 hours. The solution is concentrated in a rotary evaporator to remove tetrahydrofuran. After precipitates produced by adding toluene to the residue is filtered off on Celite, the filtrate is concentrated and dried by heating for 1 hour to obtain a Zr(salen) complex (470 mg, yield: 85%) represented by the following formula (XVII):

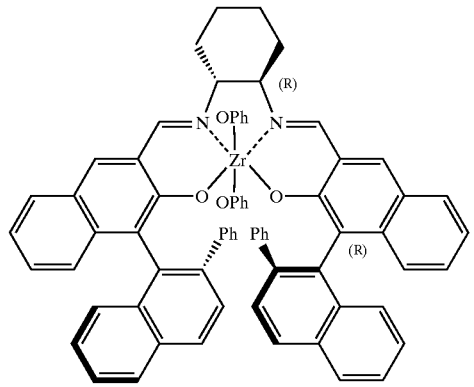

(XVII)

The elementary analysis of the thus obtained complex shows H: 5.24%, C: 76.14% and N: 2.37%, which are well coincident with theoretical values (H: 5.14%, C: 75.96%, N: 2.46%) of $C_{72}H_{54}N_2O_4Zr \cdot 2H_2O$. Also, signals inherent to the complex are observed at δ: 8.55 (s, 2H), 3.71 (p-d, J=6.0 Hz) and 2.36 (p-d, J=9.8 Hz, 2H) as measured by $^1$H-NMR (400 MHz).

Complex Synthesis Example 2

(1R, 2R)-1,2-cyclohexanediamine (made by Kankyo Kagaku Center Co., Ltd., 5.7 mg, 0.05 mmol) is dissolved into ethanol (1.0 ml). To the resulting solution is added 3,5-di-t-butyl salicylaldehyde (made by Aldrich Chem. Co., 23.4 mg, 0.1 mmol). This solution is refluxed under heating for 6 hours with stirring. After the completion of the reaction, the temperature is turned to room temperature, and the resulting precipitates are filtered and dried by heating under a reduced pressure for 1 hour. Then, the dried precipitates are dissolved into anhydrous tetrahydrofuran (1.5 ml) under a nitrogen atmosphere and added with sodium hydride (oily, about 60%)(made by Kishida Kagaku Co., Ltd., 4.4 mg, 0.11 mmol) and stirred for 1 hour The reaction solution is added with a 1:2 complex of zirconium chloride-tetrahydrofuran (made by Aldrich Chem. Co., 31.1 mg, 0.08 mmol) and further stirred for 12 hours and concentrated in a rotary evaporator to remove tetrahydrofuran. After precipitates produced by adding toluene to the resulting residue is filtered off on Celite, the filtrate is concentrated and subsequently dried by heating under a reduced pressure for 1 hour. The dried concentrate is dissolved into tetrahydrofuran (1.0 ml) under a nitrogen atmosphere. The resulting solution is added with lithium phenoxide (in 1.0M tetrahydrofuran)(made by Aldrich Chem. Co., 0.1 ml, 0.1 mmol) and stirred for 16 hours. The solution is concentrated in a rotary evaporator to remove tetrahydrofuran. After precipitates produced by adding toluene to the residue is filtered off on Celite, the filtrate is concentrated and dried by heating for 1 hour. As the residue is measured by a mass spectroscopy, the formation of a Zr(salen) complex represented by the following formula (XVIII):

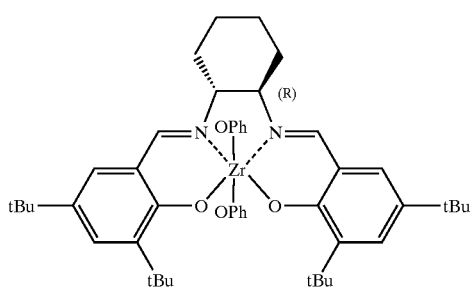

is confirmed. Moreover, a theoretical value of $C_{48}H_{62}N_2O_4Zr[M^{2+}—(OPh^-)_2+(OMe^-)]$ by EI-MS m/z is 665.3, while a found value of the thus obtained complex is 665.1. Since the measurement by the mass spectroscopy is carried out by dissolving the complex of the formula (XVIII) into methanol, it is observed that a phenoxy ion is dissociated and exchanged with methanol as the solvent to form a monomethoxide body.

Complex Synthesis Example 3

(1S, 2S)-1,2-cyclohexanediamine (made by Kankyo Kagaku Center Co., Ltd., 5.7 mg, 0.05 mmol) is dissolved into ethanol (10 ml). To the resulting solution is added (R)-3-formyl-2-hydroxy-2'-phenyl-1,1'-binaphthyl (37.4 mg, 0.1 mmol). Moreover, (R)-3-formyl-2-hydroxy-2'-phenyl-1,1'-binaphthyl is obtained by a well-known method described in H. Sakaki, R. Irie, T. Hamada, K. Suzuki and T. Katsuki, Tetrahedron, 50(41), 11827–11838 (1994) or the like. This solution is refluxed under heating for 6 hours with stirring. After the completion of the reaction, the temperature is turned to room temperature, and the resulting precipitates are filtered and dried by heating under a reduced pressure for 1 hour. Then, the dried precipitates are dissolved into anhydrous tetrahydrofuran (1.5 ml) under a nitrogen atmosphere and added with sodium hydride (oily, about 60%)(made by Kishida Kagaku Co., Ltd., 4.4 mg, 0.11 mmol) and stirred for 1 hour. The reaction solution is added with a 1:2 complex of zirconium chloride-tetrahydrofuran (made by Aldrich Chem. Co., 31.1 mg, 0.08 mmol) and further stirred for 12 hours and concentrated in a rotary evaporator to remove tetrahydrofuran. After precipitates produced by adding toluene to the resulting residue is filtered off on Celite, the filtrate is concentrated and subsequently dried by heating under a reduced pressure for 1 hour. The dried concentrate is dissolved into tetrahydrofuran (1.0 ml) under a nitrogen atmosphere. The resulting solution is added with lithium phenoxide (in 1.0M tetrahydrofuran) (made by Aldrich Chem. Co., 0.1 ml, 0.1 mmol) and stirred for 16 hours. The solution is concentrated in a rotary evaporator to remove tetrahydrofuran. After precipitates produced by adding toluene to the residue is filtered off on Celite, the filtrate is concentrated and dried by heating for 1 hour. As the residue is measured by $^1$H-NMR and a mass spectroscopy, the formation of a Zr(salen) complex represented by the following formula (XIX):

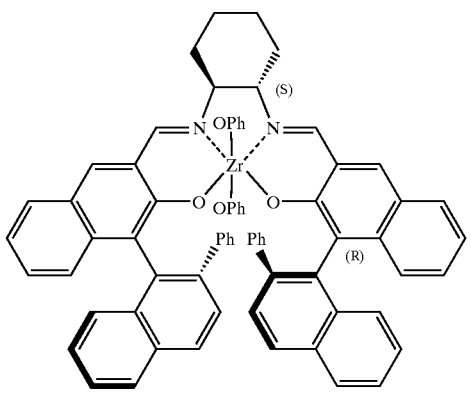

is confirmed. Also, signals inherent to the complex are observed at δ: 8.06 (s, 2H), 3.15 (p-d, J=6.0 Hz, 2H) and 1.54 (p-d, J=10.9 Hz, 2H) as measured by $^1$H-NMR (400 MHz) of the thus obtained complex. Moreover, a theoretical value of $C_{72}H_{54}N_2O_4Zr[M^{2+}—(OPh^-)^{2+}(OMe^-)]$ by EI-MS m/z is 945.3, while a found value of the thus obtained complex is 945.2. Since the measurement by the mass spectroscopy is carried out by dissolving the complex of the formula (XIX) into methanol, it is observed that a phenoxy ion is dissociated and exchanged with methanol as the solvent to form a monomethoxide body.

Complex Synthesis Example 4

(R)-(+)-1,1'-binaphthyl-2,2'-diamine (made by Aldrich Chem. Co., 14.2 mg, 0.05 mmol) is dissolved into ethanol (1.0 ml). To the resulting solution is added salicylaldehyde (made by Nakaraitesuku Co., Ltd., 12.2 mg, 0.1 mmol). This solution is refluxed under heating for 6 hours with stirring. After the completion of the reaction, the temperature is turned to room temperature, and the resulting precipitates are filtered and dried by heating under a reduced pressure for 1 hour. Then, the dried precipitates are dissolved into anhydrous tetrahydrofuran (1.5 ml) under a nitrogen atmosphere and added with sodium hydride (oily, about 60%) (made by Kishida Kagaku Co Ltd., 4.4 mg, 0.11 mmol) and stirred for 1 hour. The reaction solution is added with a 1:2 complex of zirconium chloride-tetrahydrofuran (made by Aldrich Chem. Co., 31.1 mg, 0.08 mmol) and further stirred for 12 hours and concentrated in a rotary evaporator to remove tetrahydrofuran. After precipitates produced by adding toluene to the resulting residue is filtered off on Celite, the filtrate is concentrated and subsequently dried by heating under a reduced pressure for 1 hour. The dried concentrate is dissolved into tetrahydrofuran (1.0 ml) under a nitrogen atmosphere. The resulting solution is added with lithium phenoxide (in 1.0M tetrahydrofuran) (made by Aldrich Chem. Co., 0.1 ml, 0.1 mmol) and stirred for 16 hours. The solution is concentrated in a rotary evaporator to remove tetrahydrofuran. After precipitates produced by adding toluene to the residue is filtered off on Celite, the filtrate is concentrated and dried by heating for 1 hour. As the residue is measured by a mass spectroscopy, the formation of a Zr(salen) complex represented by the following formula (XX):

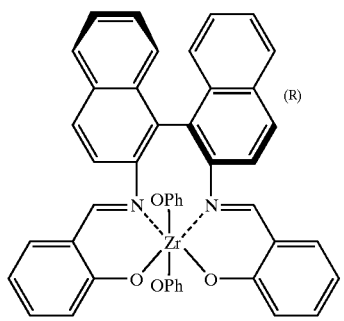

(XX)

is confirmed. Moreover, a theoretical value of $C_{45}H_{32}N_2O_4Zr[M^{2+}-(OPh^-)_2+(OMe^-)]$ by EI-MS m/z is 597.1, while a found value of the thus obtained complex is 597.1. Since the measurement by the mass spectroscopy is carried out by dissolving the complex of the formula (XX) into methanol, it is observed that a phenoxy ion is dissociated and exchanged with methanol as the solvent to form a monomethoxide body.

EXAMPLE 1

3-phenylcyclobutanone (14.6 mg, 0.1 mmol) is dissolved into dichloromethane ($CH_2Cl_2$, 1.0 ml) at room temperature (25° C.). To this solution are successively added the complex of the formula (XVII) (5.5 mg, 5.0 µmol) and urea-hydrogen peroxide adduct (UHP, 12 mg, content of hydrogen peroxide: 0.12 mmol) and the resulting mixture is stirred at room temperature for 24 hours.

The mixture is concentrated in a rotary evaporator and chromatographed on silica gel using a mixed solution of hexane and ethyl acetate (=6.5/1) as an elute to obtain β-phenyl-γ-butyrolactone (10.9 mg, yield: 68%).

As the enantiomeric excess of this product is determined by a high-speed liquid chromatography (HPLC) analysis using a Daicel Chiralpak AD-H and an elute of hexane/isopropanol (=49/1), the product is mainly composed of R-isomer and its enantiomeric excess is 87%ee as shown in Table 1.

Reference Example 1

The same procedure as in Example 1 is repeated except that the complex of the formula (XVIII) (4.1 mg, 5.0 µmol) is used instead of the complex of the formula (XVII) (5.5 mg, 5.0 µmol) to obtain results as shown in Table 1.

Reference Example 2

The same procedure as in Example 1 is repeated except that the complex of the formula (XIX) (5.5 mg, 5.0 µmol) is used instead of the complex of the formula (XVII) (5.5 mg, 5.0 µmol) to obtain results as shown in Table 1.

Reference Example 3

The same procedure as in Example 1 is repeated except that the complex of the formula (XX) (3.8 mg, 5.0 µmol) is used instead of the complex of the formula (XVII) (5.5 mg, 5.0 µmol) to obtain results as shown in Table 1.

TABLE 1

|  | Catalyst | Yield (%) | Enantiomeric excess (% ee) | Steric configuration |
|---|---|---|---|---|
| Example 1 | Formula (XVII) | 68 | 87 | R |
| Reference Example 1 | Formula (XVIII) | 20 | 23 | S |
| Reference Example 2 | Formula (XIX) | 13 | 9 | S |
| Reference Example 3 | Formula (XX) | 12 | 1 | — |

The reaction formula corresponding to Example 1 and Reference Examples 1–3 in Table 1 is shown as follows.

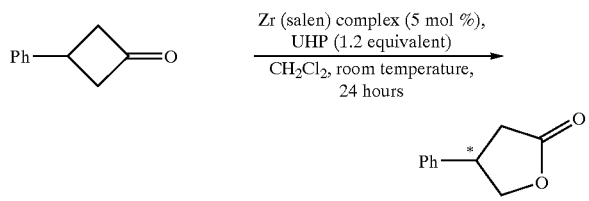

As seen from Table 1, the complex of the formula (XVII) is considerably excellent as the catalyst among the above Zr(salen) complexes in view of the catalytic activity and enantioselectivity. Also, the complex of the formula (XIX) corresponding to a diastereomer of the complex of the formula (XVII) is low in the catalytic activity and enantioselectivity, from which it is understood that a chiral binaphthyl group barfly affects the regulation of chiral conformation.

EXAMPLE 2

The same procedure is repeated except that an aqueous solution of 30% hydrogen peroxide ($H_2O_2$, 15 µl, content of hydrogen peroxide: 0.12 mmol) is used instead of the urea-hydrogen peroxide adduct (UHP, 12 mg, 0.12 mmol) to obtain results as shown in Table 2.

Reference EXAMPLE 4

The same procedure is repeated except that a solution of t-butylhydroperoxide (TBHP) in toluene (3.34 N)(30 µl, content of TBHP: 0.1 mmol) is used instead of the urea-hydrogen peroxide adduct (UHP, 12 mg, 0.12 mmol) to obtain results as shown in Table 2.

Reference Example 5

The same procedure is repeated except that bis(trimethylsilyl) peroxide (TMS-O-O-TMS, 21 mg, 0.12 mmol) is used instead of the urea-hydrogen peroxide adduct (UHP, 12 mg, 0.12 mmol) to obtain results as shown in Table 2.

TABLE 2

|  | Oxidizer | Yield (%) | Enantiomeric excess (% ee) |
|---|---|---|---|
| Example 1 | UHP | 68 | 87 |
| Example 2 | $H_2O_2$ | 60 | 56 |
| Reference Example 4 | TBHP | trace | — |

TABLE 2-continued

| | Oxidizer | Yield (%) | Enantiomeric excess (% ee) |
|---|---|---|---|
| Reference Example 5 | TMS—O—O—TMS | 11 | 4 |

The reaction formula corresponding to Example 2 and Reference Examples 4, 5 in Table 2 is shown as follows.

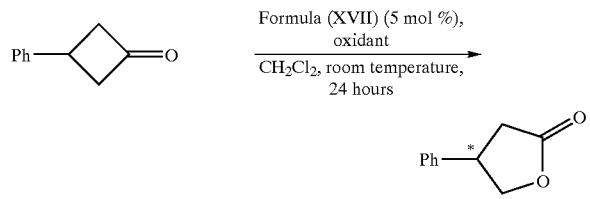

As seen from Table 2, UHP and $H_2O_2$ are excellent as an oxidizer in view of the oxidative conversion and enantioselectivity, and particularly UHP is preferable.

EXAMPLE 3

The same procedure as in Example 1 is repeated except that chlorobenzene (PhCl 1.0 ml) is used instead of dichloromethane ($CH_2Cl_2$, 1.0 ml) to obtain results as shown in Table 3.

EXAMPLE 4

The same procedure as in Example 1 is repeated except that diethylether ($Et_2O$, 1.0 ml) is used instead of dichloromethane ($CH_2Cl_2$, 1.0 ml) to obtain results as shown in Table 3.

EXAMPLE 5

The same procedure as in Example 1 is repeated except that ethanol (EtOH, 1.0 ml) is used instead of dichloromethane ($CH_2Cl_2$, 1.0 ml) to obtain results as shown in Table 3.

TABLE 3

| | Solvent | Yield (%) | Enantiomeric excess (% ee) |
|---|---|---|---|
| Example 1 | $CH_2Cl_2$ | 68 | 87 |
| Example 3 | PhCl | 80 | 85 |
| Example 4 | $Et_2O$ | 32 | 45 |
| Example 5 | EtOH | 44 | 52 |

The reaction formula corresponding to Examples 3 to 5 of Table 3 is shown as follows.

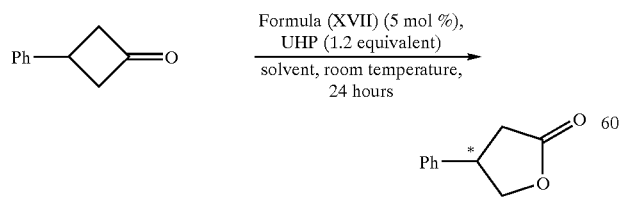

As seen from Table 3, the halogenated hydrocarbons such as $CH_2Cl_2$, PhCl and the like are excellent as a solvent in view of the yield and enantioselectivity.

EXAMPLE 6

The same procedure as in Example 1 is repeated except that the reaction is carried out at 0° C. instead of the room temperature (25° C.) to obtain results as shown in Table 4.

EXAMPLE 7

The same procedure as in Example 1 is repeated except that the reaction is carried out at 40° C. instead of the room temperature (25° C.) to obtain results as shown in Table 4.

TABLE 4

| | Temperature (° C.) | Yield (%) | Enantiomeric excess (% ee) |
|---|---|---|---|
| Example 1 | 25 | 68 | 87 |
| Example 6 | 0 | 58 | 81 |
| Example 7 | 40 | 78 | 81 |

The reaction formula corresponding to Examples 6 and 7 of Table 4 is shown as follows:

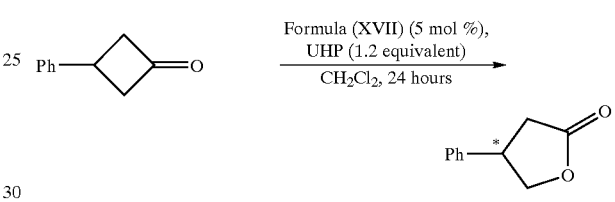

As seen from Table 4, the reaction rate rises as the temperature rises within a range of 0 to 40° C., but the enantioselectivity lowers even at a higher temperature or a lower temperature and hence the reaction temperature is preferable to be room temperature.

EXAMPLE 8

The same procedure as in Example 1 is repeated except that 3-(p-chlorophenyl)cyclobutanone (18.0 mg, 0.1 mmol) is used instead of 3-phenylcyclobutanone (14.6 mg, 0.1 mmol). As a result, β-(p-chlorophenyl)-γ-butyrolactone is obtained as a product instead of β-phenyl-γ-butyrolactone. The results are shown in Table 5. Also, the reaction formula is shown as follows.

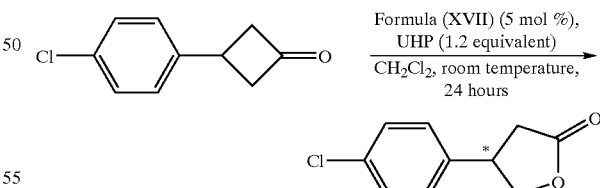
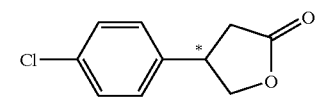

EXAMPLE 9

The same procedure as in Example 1 is repeated except that 3-(p-methoxyphenyl)cyclobutanone (17.6 mg, 0.1 mmol) is used instead of 3-phenylcyclobutanone (14.6 mg, 0.1 mmol). As a result, β-(p-methoxyphenyl)-γ-butyrolactone is obtained as a product instead of β-phenyl-γ-butyrolactone. The results are shown in Table 5. Also, the reaction formula is shown as follows.

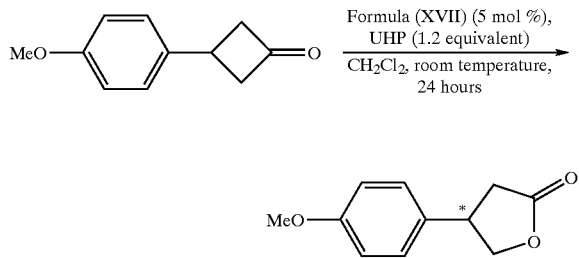

EXAMPLE 10

The same procedure as in Example 1 is repeated except that 3-octylcyclobutanone (18.2 mg, 0.1 mmol) is used instead of 3-phenylcyclobutanone (14.6 mg, 0.1 mmol). As a result, β-octyl-γ-butyrolactone is obtained as a product instead of β-phenyl-γ-butyrolactone. The results are shown in Table 5. Also, the reaction formula is shown as follows.

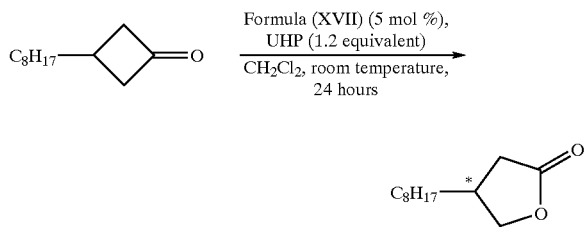

EXAMPLE 11

The same procedure as in Example 1 is repeated except that a compound of the formula (VII) (10.6 mg, 0.1 mmol) is used instead of 3-phenylcyclobutanone (14.6 mg, 0.1 mmol). As a result, a compound of the formula (XII) is obtained as a product instead of β-phenyl-γ-butyrolactone. The results are shown in Table 5 Also, the reaction formula is shown as follows.

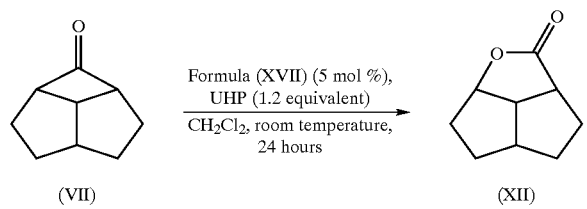

TABLE 5

| | Substrate | Yield (%) | Enantiomeric excess (% ee) |
|---|---|---|---|
| Example 1 | Formula (V) $R^1$ = Ph | 68 | 87 |
| Example 8 | Formula (V) $R^1$ = p-ClC$_6$H$_4$ | 63 | 82 |

TABLE 5-continued

| | Substrate | Yield (%) | Enantiomeric excess (% ee) |
|---|---|---|---|
| Example 9 | Formula (V) $R^1$ = p-MeOC$_6$H$_4$ | 43 | 84 |
| Example 10 | Formula (V) $R^1$ = n-C$_8$H$_{17}$ | 63 | 81 |
| Example 11 | Formula (VII) | 99 | 94 |

As seen from Table 5, the production method according to the invention can be applied to various cyclic ketones and also the high enantiomeric excess of not less than 80%ee can be obtained.

EXAMPLE 12

A racemic bicyclo[4.2.0]octan-7-one (12.4 mg, 0.1 mmol) is dissolved into chlorobenzene (PhCl, 1.0 ml) at room temperature (25° C.). To the resulting solution are successively added the complex of the formula (XVII) (8.8 mg, 8.0 μmol), urea-hydrogen peroxide adduct (UHP, 12 mg, content of hydrogen peroxide: 0.12 mmol) and bicyclohexyl (internal standard for the calculation of conversion), and then the resulting mixture is stirred at room temperature for 2 hours.

The resulting product is analyzed through a gas-liquid chromatography (GLC) using an optically active column (SUPELCO BETA-DEX-255) to measure a conversion of bicyclo[4.2.0]octanon-7-one, yield of formulae (XIII) and (XVI) and yield of formulae (XIV) and (XV). As a result, the conversion is 66%, and the yield of formulae (XIII) and (XVI) is 48% and the yield of formulae (XIV) and (XV) is 18%. The results are shown in Table 6.

Further, the product is analyzed through the gas-liquid chromatography using an optically active column (SUPLEC BETA-DEX-255) to measure an enantiomeric excess of formulae (XIII) and (XVI) and an enantiomeric excess of formulae (XIV) and (XV). As a result, the enantiomeric excess of formulae (XIII) and (XVI) is 85%ee in which the formula (XIII) is main, while the enantiomeric excess of formulae (XIV) and (XV) is not less than 99%ee in which the formula (XV) is trace. The results are shown in Table 6.

The relative reaction ratio $k_{rel}$ between the cyclic ketone of the formula (VIII) and the cyclic ketone of the formula (VIX) is 3.5 as calculated according to the Kagan's equation.

EXAMPLE 13

The same procedure as in Example 12 is repeated except that the stirring time is changed into 2.5 hours to obtain results as shown in Table 6.

EXAMPLE 14

The same procedure as in Example 12 is repeated except that the stirring time is changed into 3 hours to obtain results as shown in Table 6.

TABLE 6

| | Substrate | | | Formulae (XIII) and (XVI) | | Formulae (XIV) and (XV) | |
|---|---|---|---|---|---|---|---|
| | Conversion (%) | Enantiomeric excess (% ee) | $k_{rel}$ | Yield (%) | Enantiomeric excess (% ee) | Yield (%) | Enantiomeric excess (% ee) |
| Example 12 | 66 | 63 | 3.5 | 48 | 85 | 18 | >99 |
| Example 13 | 76 | 82 | 3.8 | 53 | 85 | 23 | >99 |
| Example 14 | 80 | 93 | 4.5 | 56 | 83 | 24 | >99 |

The reaction formula corresponding to Examples 12 to 14 of Table 6 is shown as follows.

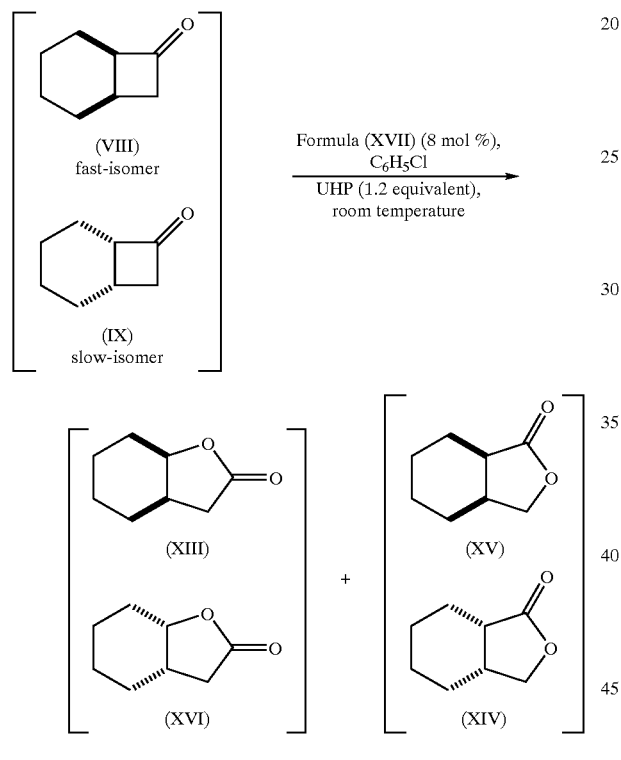

As seen from Table 6, the relative reaction ratio $k_{rel}$ between the cyclic ketone of the formula (VIII) and the cyclic ketone of the formula (IX) in all of Examples 12 to 14 is about 4, so that the reaction rate of the cyclic ketone of the formula (VIII) is faster than that of the cyclic ketone of the formula (IX). Since the reaction rate largely differs between the cyclic ketones, it is possible to kinetically divide the racemic mixture by applying the production method according to the invention. In all of Examples 12 to 14, the compound of the formula (XV) is only obtained in a trace amount, and the compound of the formula (XIII) is exclusively obtained from the cyclic ketone of the formula (VIII), and the compounds of the formulae (XVI) and (XIV) are obtained from the cyclic ketone of the formula (IX) at a ratio of about 1:6.

As mentioned above, according to the invention, optically active lactone enantiomers can be produced from various cyclic ketones in a high enantioselectivity. Also, the invention can provide catalysts suitable for producing the optically active lactone from the cyclic ketone. Therefore, the complexes according to the invention and the method of producing the same are particularly useful for the synthesis of pharmaceutical and agricultural chemicals.

What is claimed is:

1. A method of producing an optically active lactone compound, which comprises using a Zr(salen) complex represented by the following formula (I) or (II):

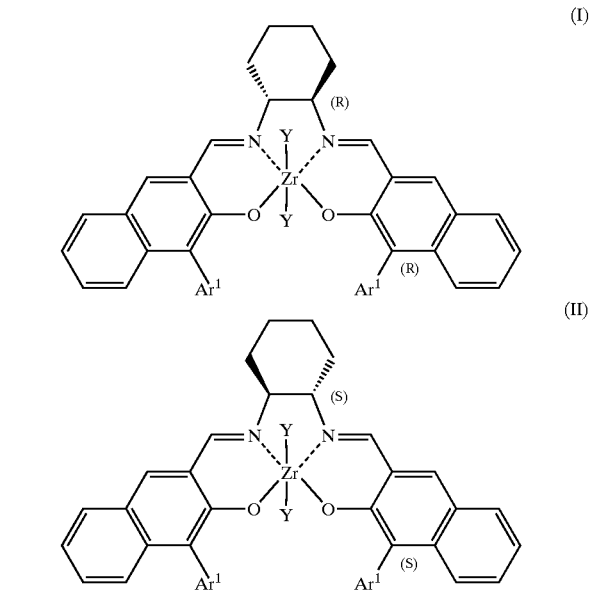

wherein $Ar^1$ is an aryl group having a carbon number of 10 to 16 and Y is a phenoxy group or an alkoxy group having a carbon number of 1 to 10 as a catalyst in a solvent, and conducting a Baeyer-Villiger reaction of a cyclic ketone compound with at least one oxidizer selected from the group consisting of hydrogen peroxide, aqueous hydrogen peroxide and urea-hydrogen peroxide adduct.

2. The method according to claim 1, wherein the Zr(salen) complex is represented by the following formula (III) or (IV):

(III)

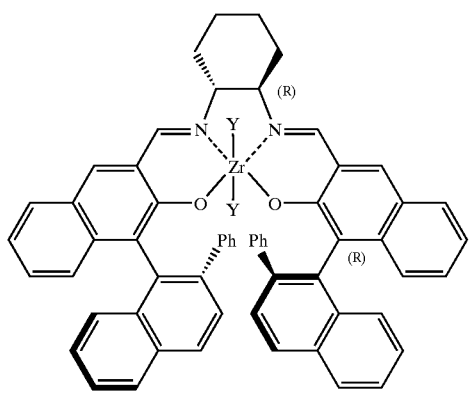

(IV)

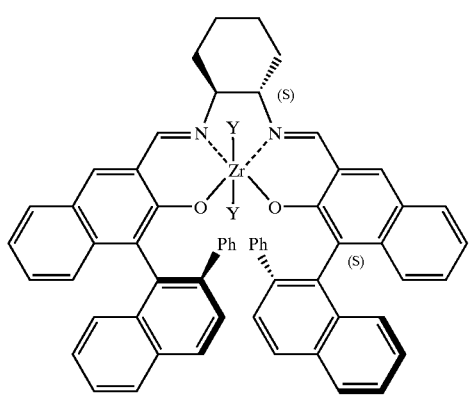

wherein Ph is a phenyl group and Y is a phenoxy group or an alkoxy group having a carbon number of 1 to 10.

3. The method according to claim 1, wherein the symbol Y is a phenoxy group.

4. The method according to claim 1, wherein the cyclic ketone compound is represented by the following formula (V), (VI), (VII), (VIII) or (IX):

(V)

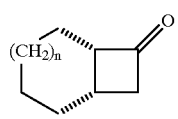

wherein $R^1$ is a substituted or non-substituted alkyl group having a carbon number of 1 to 20 or a substituted or non-substituted aryl group having a carbon number of 6 to 15, (VI)

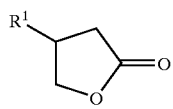

wherein $R^2$ is a substituted or non-substituted alkyl group having a carbon number of 1 to 20 or a substituted or non-substituted aryl group having a carbon number of 6 to 15, (VII)

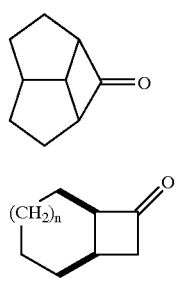

(VIII)

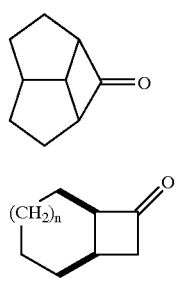

wherein n is 0, 1 or 2, (IX)

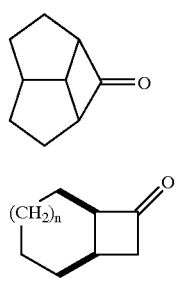

wherein n is 0, 1 or 2.

5. The method according to claim 4, wherein the cyclic ketone compound is 3-phenyl cyclobutanone, 3-(p-chlorophenyl) cyclobutanone, 3-(p-methoxyphenyl) cyclobutanone or 3-octyl cyclobutanone.

6. The method according to claim 1, wherein the lactone compound is represented by the following formula (X), (XI), (XII), (XIII), (XIV), (XV) or (XVI):

(X)

wherein $R^1$ is a substituted or non-substituted alkyl group having a carbon number of 1 to 20 or a substituted or non-substituted aryl group having a carbon number of 6 to 15, (XI)

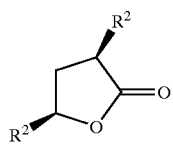

wherein $R^2$ is a substituted or non-substituted alkyl group having a carbon number of 1 to 20 or a substituted or non-substituted aryl group having a carbon number of 6 to 15, (XII)

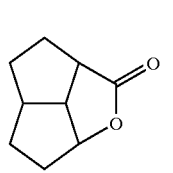

(XIII)

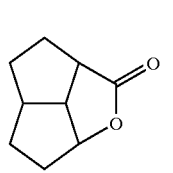

wherein n is 0, 1 or 2,

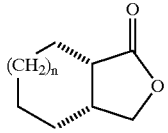
(XIV)

wherein n is 0, 1 or 2,

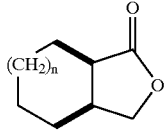
(XV)

wherein n is 0, 1 or 2,

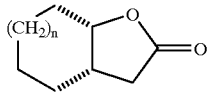
(XVI)

wherein n is 0, 1 or 2.

7. The method according to claim 6, wherein the lactone compound is β-phenyl-γ-butyrolactone, β-(p-chlorophenyl)-γ-butyrolactone, β-(p-methoxyphenyl)-γ-butyrolactone or β-octyl-γ-butyrolactone.

8. The method according to claim 1, wherein the solvent is a halogenated hydrocarbon.

9. The method according to claim 8, wherein the halogenated hydrocarbon is dichloromethane or chlorobenzene.

10. The method according to claim 1, wherein the oxidizer is a urea-hydrogen peroxide adduct.

11. The method according to claim 1, wherein the optically active lactone compound has an enantiomeric excess of not less than 80% ee.

12. A Zr(salen) complex represented by the following formula (I) or (II):

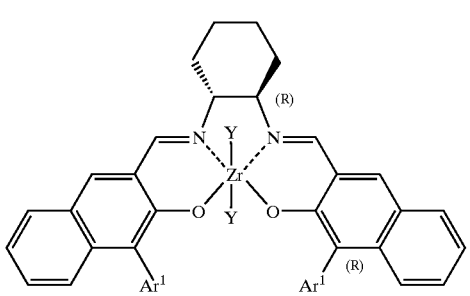
(I)

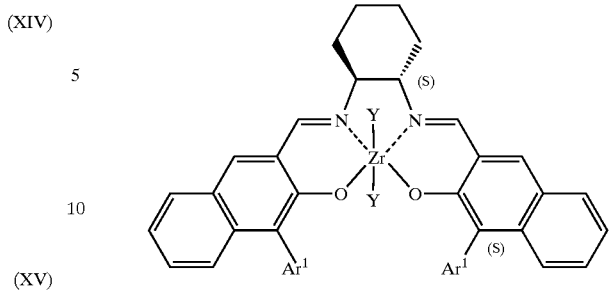
(II)

wherein $Ar^1$ is an aryl group having a carbon number of 10 to 16 and Y is a phenoxy group or an alkoxy group having a carbon number of 1 to 10.

13. A Zr(salen) complex according to claim 12, wherein the complex is represented by the following formula (III) or (IV):

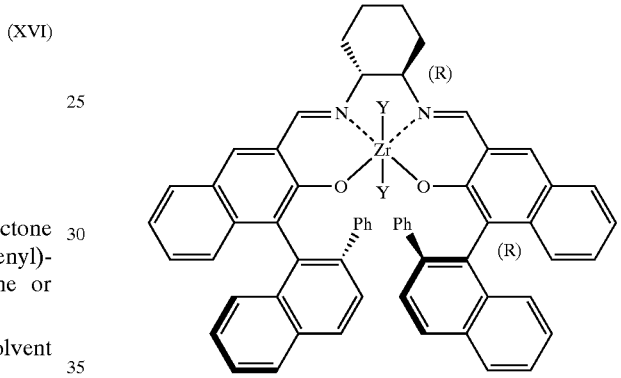
(III)

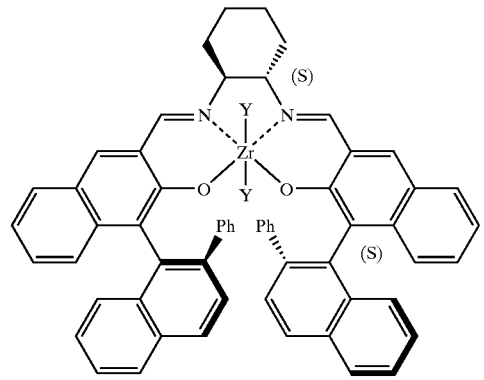
(IV)

wherein Ph is a phenyl group and Y is a phenoxy group or an alkoxy group having a carbon number of 1 to 10.

14. A Zr(salen) complex according to claim 12, wherein the symbol Y is a phenoxy group.

15. The method according to claim 2, wherein the symbol Y is a phenoxy group.

16. A Zr(salen) complex according to claim 13, wherein the symbol Y is a phenoxy group.

* * * * *